United States Patent [19]

Dervieux

[11] Patent Number: 4,823,810
[45] Date of Patent: Apr. 25, 1989

[54] BIPOLAR ELECTRODES DISCHARGING SPARKS OF PIEZO-ELECTRIC ORIGIN FOR THE RELIEF OF PAINS AND CONTRACTURES BY DIRECT APPLICATION TO THE SKIN

[76] Inventor: Dominique Dervieux, Villa Lou Miou Roc, Lieu dit des Cabanes, 06790 Aspremont, France

[21] Appl. No.: 159,418

[22] Filed: Feb. 4, 1988

Related U.S. Application Data

[63] Continuation of Ser. No. 835,867, Apr. 19, 1986, abandoned.

[51] Int. Cl.$^4$ .............................................. A61N 1/02
[52] U.S. Cl. .................................... 128/783; 128/800
[58] Field of Search ............... 128/783, 800, 801, 735, 128/907, 303.14, 303.17; 310/339

[56] References Cited

U.S. PATENT DOCUMENTS

| | | |
|---|---|---|
| 4,043,342 | 8/1977 | Morrison, Jr. ................. 128/303.14 |
| 4,082,087 | 4/1978 | Housson ............................. 128/640 |
| 4,112,923 | 9/1978 | Tomecek ........................ 128/735 X |

FOREIGN PATENT DOCUMENTS

| | | |
|---|---|---|
| 65169 | 1/1956 | France . |
| 2500745 | 9/1982 | France . |

*Primary Examiner*—Lee S. Cohen
*Attorney, Agent, or Firm*—Young & Thompson

[57] ABSTRACT

Bipolar electrodes discharge sparks of piezoelectric origin. The poles (4, 5) of the electrodes are less than a centimeter apart in order to avoid a double discharge and to provide better stimulation. A separation device (7) is placed between them; this device is substantially longer than the length of the electrodes (4, 5) so as automatically to distance the electrodes from the skin. This separation device also serves as insulation to prevent interdischarge of the electrodes.

7 Claims, 2 Drawing Sheets

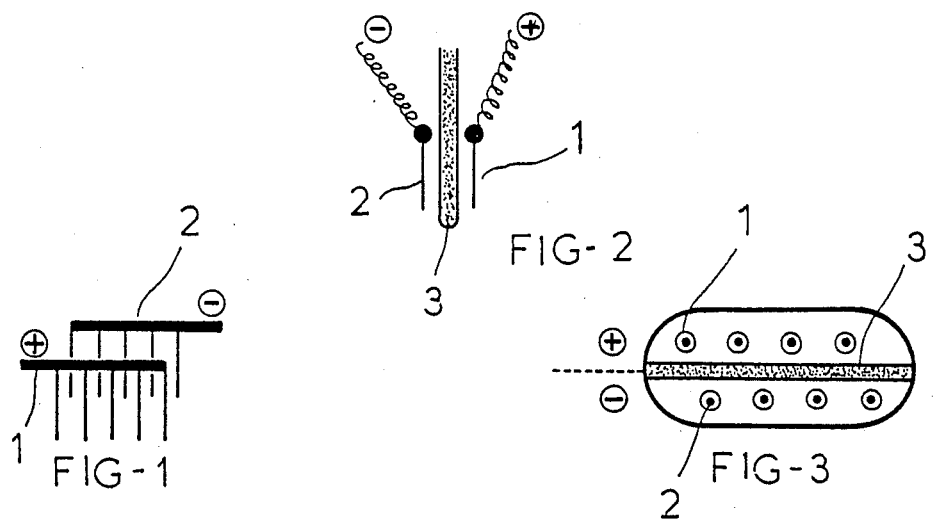
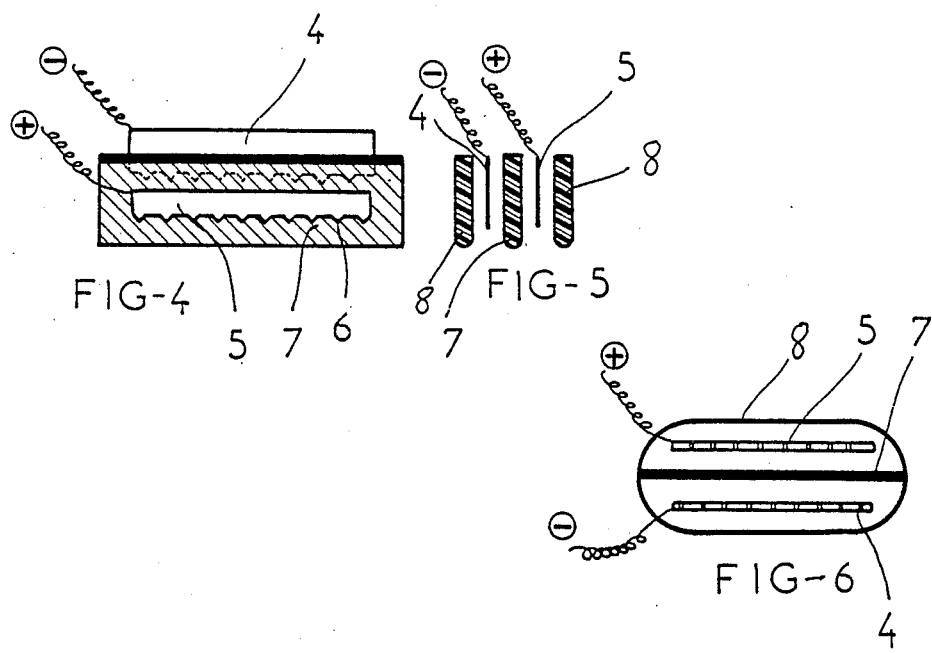
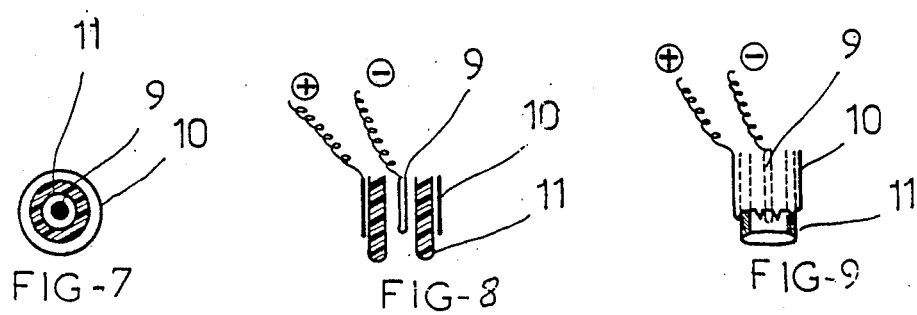

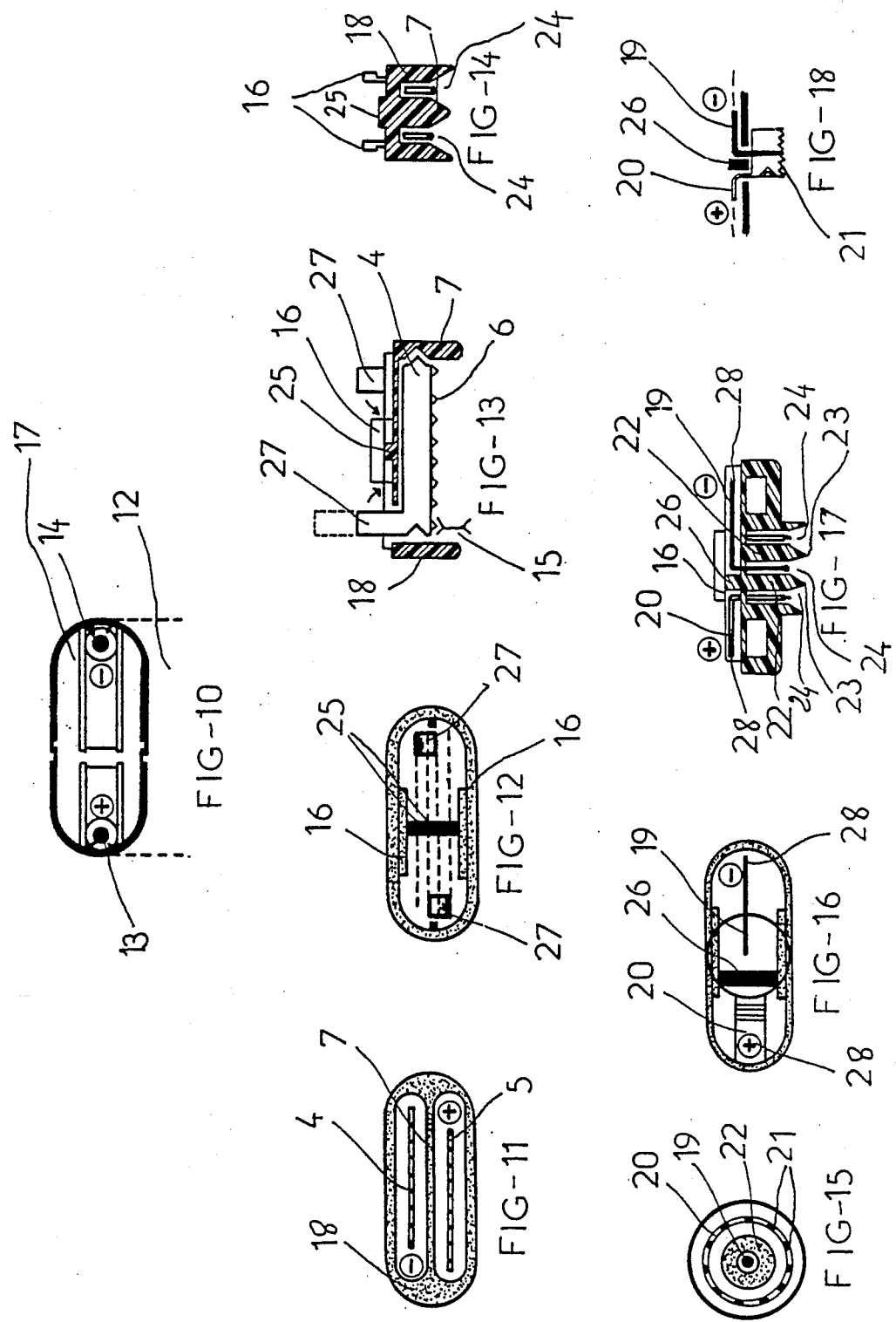

BIPOLAR ELECTRODES DISCHARGING SPARKS OF PIEZO-ELECTRIC ORIGIN FOR THE RELIEF OF PAINS AND CONTRACTURES BY DIRECT APPLICATION TO THE SKIN

This application is a continuation of application Ser. No. 835,867, filed Apr. 10, 1986, now abandoned.

BACKGROUND OF THE INVENTION

The object of the invention is bipolar electrodes discharging sparks of piezoelectric origin for the relief of pains and contractures by direct application to the skin.

The electrodes used at present are unipolar electrodes. The piezoelectric generator must therefore be grounded. This situation may present some drawbacks: risk of shock owing to poor contact with the user at ground level; risk of shock when a third person using the apparatus to treat the patient, is in contact with it; little effectiveness on pains and contractures.

These apparatus are, in general, used for acupuncture. Before making use of the electrodes, the required points of acupuncture must be located.

SUMMARY

The invention tends to resolve these technical problems and, in its application, aims notably at bringing about pain-killing and relaxing effects, both for humans and animals.

Characteristic of the electrodes according to the invention is that they use piezoelectric current. The said piezoelectric current is used for the discharge of sparks. The piezoelectric current can be three thousand volts in peaks (about one to ten thousand volts) of some tenths of milli-seconds, of 0.05 milli-amperes under pressure and 1 milli-ampere when releasing the operating handle of the piezoelectric generator between the two poles of the electrode. The current is positive on one of the poles of the electrode and negative on the other pole of the electrode by simultaneous discharges. The polarisation reverts between pressure and release.

The electrodes according to the invention are bipolar. One pole is linked to the outlet of the piezoelectric generator (insulated outlet), and the other pole is linked to the frame of the piezoelectric generator (outlet in contact with the other pole of the crystal(s)).

The electrodes, which have electric conducting properties, are formed with points of discharge of sparks, either fixed points on a support (serrated points on a blade, reliefs on any support, brush . . . ) of one to several tens per pole, or separate points, or of a single plate, blade or bar.

The poles of the said electrodes are less than one centimeter apart (generally a few centimeters maximum) so as to prevent the feeling of double shock and provide better stimulation.

A separation device is placed between the two poles of the electrodes.

The said separation device is a few tenths of a millimeter longer than the length of the points of the electrodes, so that the electrodes are a few tenths of a millimeter away from the skin when the apparatus is applied to the skin.

The said separation device is made of insulating material to prevent the interdischarge of the poles.

The said separation device can open out leaving about a millimeter of the pole (or of a part of a pole of discharge, for example a point) projecting from the opening of the bell-mouth, thus allowing a cone of possible discharges.

Another characteristic of the electrodes is their shape which gives them specific advantages:

electrodes with blades with several points or needles; there are two blades or two rows of parallel needles, divided by an insulating separation device, ring-shaped electrodes with several points; there is a central point composed of one or more points or even of a ring, an insulating separation ring and a concentric outer ring with several points.

The electrodes with blades with several points or rows of parallel needles have a pain-killing and reflex action.

The ring-shaped electrodes with several points have a relaxant and trophic action.

The attached drawings given by way of non-limiting example will enable an easy understanding of the invention. They show preferred embodiments according to the invention.

BRIEF DESCRIPTION OF THE DRAWING

FIG. 1 is a perspective view of a bipolar electrode with needles, without the separator.

FIG. 2 is an end view of the bipolar electrode with needles, seen at the level of the two needles (one of each of the poles of the electrode);

FIG. 3 is a front-view of the bipolar electrode with needles.

FIG. 4 is a perspective view of a bipolar electrode with a blade with serrated points.

FIG. 5 is a view in cross-section of a bipolar electrode with a blade with serrated points.

FIG. 6 is a front view of a bipolar electrode with a blade with serrated points.

FIG. 7 is a view of a bipolar electrode, seen from the front and in section.

FIG. 8 is a view of a bipolar electrode seen in cross-section.

FIG. 9 is a view of a bipolar electrode seen in cross-section showing the external "ring-shaped" pole.

FIG. 10 is a view of the branching of the frame of the piezoelectric generator, seen from the front.

FIG. 11 is a view of the electrode with blades with several serrated points seen from the front.

FIG. 12 is a view of the electrode with parallel blades with several serrated points seen from behind.

FIG. 13 is a view of the electrode with blades with several serrated points seen in section along the longitudinal axis of one of the two blades.

FIG. 14 is a view of the electrode with blades with several serrated points seen in section along the transverse axis of the blades.

FIG. 15 is a view of the ring-shaped bipolar electrode seen from the front.

FIG. 16 is a view of the ring-shaped bipolar electrode seen from behind.

FIG. 17 is a view of the ring-shaped bipolar electrode seen lengthwise.

FIG. 18 is a view of the ring-shaped bipolar electrode seen from the two poles of the ring-shaped electrode.

DETAILED DESCRIPTION

In FIGS. 1, 2 and 3 which show a bipolar electrode with needles whose shape is designed for pain-killing and reflex action, the electrodes 1 and 2 are placed in two parallel planes.

An insulating separation device 3 is placed between the said electrodes 1 and 2.

This separation partition 3, made of insulating material, is several tenths of a millimeter longer than the length of the poles of the electrode 1 and 2. The separation partition 3 is adapted to contact the skin of the patient and thus prevents the interdischarge of the poles. This separation partition enables the distancing of the poles from the skin about two to three tenths of a millimeter (from a few tenths of a millimeter to about ten millimeters).

In FIGS. 4, 5 and 6 the bipolar electrodes 4, 5 with a blade with serrated points 6 are shown. Their shape is also designed for pain-killing action. It is of course possible to provide each pole of the electrode with one or more blades with serrated points 6.

The separation partition 7, made of insulating material, must be placed between the two blades of the electrodes 4, 5 in a parallel plane. This separation partition 7 can also surround the whole of the head of the appliance in the form of a partition 8 and in this way be part of the body of the electrode in one single piece.

FIGS. 7, 8 and 9 show a ring-shaped bipolar electrode 9, 10 with serrated points whose specific ring-shape is designed for relaxant and trophic action.

The central pole 9 of the electrode is surrounded by a separation partition made of insulating material 11, itself surrounded by another coaxial ring which is the other pole 10 of the ring-shaped electrode.

The separation partition 11, made of insulating material, is a few millimeters longer than the poles of the electrode 9 and 10. This separation partition 11 is adapted to contact the skin and in this way prevents the interdischarge of the poles. This separation partition enables the distancing of the poles from the skin, about two to three tenths of a millimeter (of a few tenths of a millimeter to ten millimeters) as with the electrode with parallel blades.

FIG. 10 is a view of the branching of the body 12 of the piezoelectric generator, with a view of the positive pole 13 and the negative pole 14; the distance between them prevents any interdischarge. One pole is linked to the outlet of the piezoelectric generator (insulating outlet), and the other pole is linked to the frame of the piezoelectric generator (outlet in contact with the other pole or the crystal(s)). The polarisation reverts between the depression and release of the lever of the generator.

FIGS. 11, 12, 13 and 14 show an electrode with blades 4, 5 with serrated points 6. Note the distance 15 which exists between the length of the insulating separation partition 7 and the points 6 of the poles 4, 5 of the electrode with blades.

Detachable fixing devices 16 enable the electrodes to be fixed and kept connected to the reception head 17 of the body of the piezoelectric generator 12.

The serrated points 6 of the blades of the electrode go beyond the opening of the bell-mouth of the separation partition 7 and of the insulating body 18 of the electrode by about one millimeter, at the level of an outwardly-opening slit, to allow a cone of discharge 24.

FIGS. 12, 13 and 14 show the separation 25 which prevents a discharge between the poles 4 and 5 at the level of their posterior contact blade 27 which is curved. These posterior contact blades 27 allow the branching of the electrode with the two outlets 13, 14 of the piezoelectric generator. All types of branching can be carried out between the electrodes and the outlets of the piezoelectric generator provided that insulation is total.

FIGS. 15, 16 17 and 18 show a bipolar electrode with two poles 19,20 (ring-shaped with serrated points).

In the embodiment shown, there are eight points 21. In this example, it is the extremity 23 of the partitions 22 made of insulating material which serves as a cone of discharge.

FIGS. 16, 17 and 18 show the separation 26 which prevents a discharge between the poles 19, 20, here very close together at the level of their posterior outlet which is curved in order to be connected at their extremity 28 with the two outlets 13, 14 of the piezoelectric generator.

The object of the invention is:

Specific bipolar electrodes: with close poles requiring particular insulation and producing a discharge of sparks of piezoelectric origin for the relief of pains and contractures.

The bipolar electrodes for the relief of pains and the stimulation of the reflex zones:

They use a neurophysiological means of action: the Transcutaneous Neuro-Stimulation (TCNS), peripheral electrostimulation having an inhibitory action on the cells of medullary relays activated by noxious flux (stimulation of sensitive nervous fibres of large diametre: $A, \alpha, \beta$) as well as the release of a secretion of endorphins.

The typical electrode can be defined thus:

at least two blades (or two rows of several needles) equipped with several serrated points (optimum eight).

These points (or needles) will be shifted from one pole of the electrode in comparison with the other one to allow a better sweep (one discharge peak every one to ten millimeters on average);

They will be connected separately to the two outlets of the piezoelectric generator (outlet and frame of the generator.)

They will be separated by a partition made of insulating material (plastic or other) which will be adapted to contact the skin (to prevent a discharge between the two poles);

This separation partition, and if necessary the body of the electrode, will enable the distance of the points of discharge of the two poles to be kept between one and ten millimeters approximately (two to three millimeters on average), this separation partition and if necessary the neutral body of the electrode being in direct contact with the skin during the use of the electrode.

The points of the two poles will appear and extend by one millimeter in a cone or slit opening out to allow for a cone of discharge. This opening out is provided for between the different separations and the body of the electrode.

The apparatus equipped with electrodes according to the invention is used as follows:

Systematic bombarding of a piezoelectric sparks of a painful or extended or connected area or a reflex dermatom going extensively beyond this area (five to ten centimeters around) from a few seconds to several minutes (optimum: twenty to forty seconds) by permanent displacement (sweeping) of the electrode (always in movement) in all directions, without systematization.

Bipolar electrodes with relaxant and trophic action:

Another aim of the invention is to stimulate muscular "motor-ends" through the skin by the "ring-shaped" bipolar electrode to provide a relaxant and trophic action.

The regulation of tonus and the suppression of contractures by the "γ" loop is used through piezoelectric discharges on the "motor-end plates" or "motor-ends". A trophic effect is also obtained by this same stimulation.

Description of the typical electrode with relaxant and trophic action:

a central metallic needle (rounded or sharpened) connected to one of the branchings;

a circular peripheral metallic "ring" with serrated points (two to ten; optimum: 8; the same part as for the poles of the "pain-killing" electrode can be used, but rolled in a cylinder) linked to the other electric branching;

a coaxial cylindrical separation device, made of an insulating material, should be placed in contact with the skin to prevent the discharge between the two poles of the electrode and enable the distancing of the poles of about two to four tenths of a millimeter (three tenths of a millimeter optimum; two tenths of a millimeter for the "ring" and three tenths of a millimeter for the central electrode would allow an increased discharge);

the points of the two poles will appear, for about a millimeter at the opening of a cone or a bell-shaped slit to create a discharge cone.

The operation of the apparatus equipped with the said electrodes is the following:

Reflex zones or muscles are stimulated at the "motor-ends" by piezoelectric discharges, by a slight circular rotating movement around the axis of the electrode without displacing the latter, for between a few seconds or several tens of seconds (rarely more than twenty), only at the level of the "motor-end" which will have been located by a few stimulations in displacing the electrode.

The complete system includes a body containing the piezoelectric generator and can be fitted, at its head, with a fixed electrode or several bipolar detachable electrodes according to the means of attachment 16.

The electrode will thus be displaced with the body of the apparatus, and the latter will be equipped with an operating lever for the piezoelectric generator that is totally electrically insulated.

I claim:

1. In an apparatus for the relief of pain and contractures by direct application to skin, comprising a piezoelectric generator having actuating means and at least one discharge electrode operatively connected to said piezoelectric generator, the improvement in which: said at least one discharge electrode is a bipolar electrode having coextensive elongated parallel positive and negative poles in closely spaced relation less than one centimeter apart, the length of the poles being substantially greater than the distance between them; and an insulating partition adapted to contact the skin of a patient to be treated, said partition extending between said positive and negative poles and projecting a substantial distance beyond said positive and negative poles sufficient to maintain said positive and negative poles spaced from the skin to which said apparatus is applied with said partition in contact with the skin.

2. Apparatus according to claim 1, and a body encircling said discharge electrode, said body being integral with said partition.

3. Apparatus according to claim 2, wherein said body projects beyond said positive and negative poles the same said substantial distance as said partition.

4. Apparatus according to claim 1, wherein each said positive and negative pole is a planar array of parallel, spaced, needle-shaped projections, and said partition is planar and parallel to said positive and negative poles.

5. Apparatus according to claim 1, wherein said positive and negative poles are plate-shaped, each comprising a series of saw-toothed discharge projections.

6. Apparatus according to claim 1, wherein said substantial distance is from a few tenths of one millimeter to ten millimeters.

7. Apparatus according to claim 1, wherein said substantial distance is 2 to 3 mm.

* * * * *